United States Patent [19]

Callahan et al.

[11] Patent Number: 4,810,778

[45] Date of Patent: Mar. 7, 1989

[54] INTERMEDIATES FOR PREPARING 1,6-DICARBA-VASOPRESSIN COMPOUNDS

[75] Inventors: James F. Callahan, Philadelphia; William F. Huffman, Malvern; Kenneth A. Newlander, West Chester; Nelson C. F. Yim, Ambler, all of Pa.

[73] Assignee: SmithKline Beckman Corporation, Philadelphia, Pa.

[21] Appl. No.: 191,673

[22] Filed: May 9, 1988

Related U.S. Application Data

[60] Division of Ser. No. 43,658, Apr. 28, 1987, Pat. No. 4,760,052, and a continuation-in-part of Ser. No. 819,336, Jan. 16, 1986, abandoned.

[51] Int. Cl.$^4$ ................................................ C07K 7/06
[52] U.S. Cl. ...................................... 530/328; 530/332
[58] Field of Search ................................ 530/328, 332

[56] References Cited

U.S. PATENT DOCUMENTS 4,760,052 7/1988 Callahan et al. ..................... 514/807

Primary Examiner—Delbert R. Phillips
Attorney, Agent, or Firm—Janice E. Williams; Stuart R. Suter; Alan D. Lourie

[57] ABSTRACT

New compounds which have potent $V_2$-vasopressin antagonistic activity are prepared by a 1,6-cyclization using peptide bond formation. The structures of the compounds are characterized by the Pas$^{1,6}$ or Tas$^{1,6}$ cyclized unit. Also a chiral synthesis of the optically pure Pas intermediates is described.

6 Claims, No Drawings

INTERMEDIATES FOR PREPARING 1,6-DICARBA-VASOPRESSIN COMPOUNDS

This is a divisional of application Ser. No. 043,658 filed Apr. 28, 1987, now U.S. Pat. No. 4,760,052.

This invention relates to new vasopressin compounds whose structures are distinguished by having a 1,6-dicarba bridge which is combined with a spirocycloalkyl substituent at the 1-position and to pharmaceutical compositions of these compounds and their use as vasopressin antagonists. The compounds have potent in vivo and in vitro vasopressin antagonist activity.

BACKGROUND OF THE INVENTION

Examples of the dithia or vasopressin antagonist art are U.S. Pat. Nos. 4,469,679, 4,481,193, 4,481,194 and 4,491,577.

Carba analogues of oxytocin and vasopressin, which have agonist activity, have been repeatedly reported in the prior art, such as in U.S. Pat. Nos. 3,980,631, 4,285,858, 4,482,486, 4,237,119 as well as in F. Fahrenholz et al., Biochem. Biophys. Res. Com. 122, 974 (1984) and J. Biol. Chem. 258 14861 (1983). Dicarba or 1,6 amino-suberic acid analogs of lisine and arginine-vasopressin and oxytocin have been reported to have variable agonist activity. These prior art structures have no substituent on the 1,6 suberic acid and are agonists, i.e. they have the same biological activity as do vasopressin (VSP) or oxytocin (OXT).

We have now found that, when the 1-unit and the dithia connection of certain vasopressin structures is replaced by a 6,6 spiroalkylenesuberic acid, the resulting compounds have potent, even enhanced antagonist activity, especially aguaretic activity.

In the description herein and in the claims, the nomenclature common in the art of peptide and vasopressin chemistry is used. When no configuration is noted, the amino acid unit is in the L, or naturally occurring, form.

Certain of the peptide art designations used herein are the following: Pas, 6,6 cyclopentamethylene-2-aminosuberic acid; Tas, 6,6 cyclotetramethylene 2-aminosuberic acid; Pas(Bzl), ω-benzyl ester of Pas; Abu, α-amino n butyric acid; Cad, cadaverine; Chg, cyclo-hexylglycine; Cha, cyclohexylalanine; Thr, threonine; Pba, α-aminophenylbutyric acid; Gln, glutamic acid amide or glutamine; Pro, proline, ΔPro, Δ³-proline; Gly, glycine; Tyr, tyrosine; Tyr(Alk), lower alkyl ether of Tyr; Phe, phenylalanine; Phe(4'Alk), 4'-alkylphenylalanine; MeAla, N-methylalanine; Val, valine; Ile, isoleucine; Nle, norleucine; Leu, leucine; Ala, alanine; Lys, lysine; Arg, arginine; HArg, homoarginine; MeArg, N-methylarginine; MeHArg, N-methylhomoarginine; MeLys, N-methyllysine; Met, methionine; Asn, asparagine; Put(G), 1-amino 4 guanidinobutane (—NH(CH$_2$)$_4$.NHC(NH)$_4$NH$_2$); Glu, glutamic acid; Orn, ornithine; Asp, aspartic acid, MeOrn, N-methylornithine; Tos, tosylate; BHA, benzhydrylamine; DMAP, 4-dimethylaminopyridine; DIEA, diisopropylethylamine; Trp, tryptophan; HF, hydrogen fluoride; 4-MeBzl, 4-methylbenzyl; TFA, trifluoroacetic acid; DCC, dicyclohexylcarbo diimide; Boc, t-butyloxycarbonyl; Z, benzyloxycarbonyl; VSP, vasopressin; HBT, hydroxybenzotriazole. In the definitions such as MeArg above, Me denotes a methyl located on the amido nitrogen of the peptide unit concerned. The designation, Pas$^{1,6}$, is used to denote the cyclized peptide as described hereafter. "Alk" represents a lower alkyl of 1–4 carbons. For example, these may be optionally attached to the oxygen substituent of a tyrosine unit at position 2 of the peptide of formula I, to the N-terminal nitrogen of the tail, or to the 4'-position of a Phe unit at position 2 or 3 of the peptide of formula I. Such alkyl substituents include methyl, ethyl, n-propyl, isopropyl or butyl. Ethyl is preferred. When the term "vasopressin" is used, it means L-arginine vasopressin (AVP) unless otherwise modified.

DESCRIPTION OF THE INVENTION

The dicarba-vasopressin compounds of this invention are illustrated by the following structural formula:

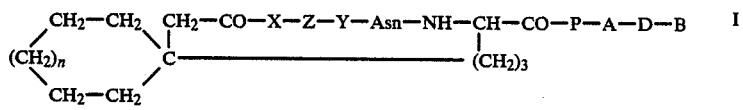

in which:

n is 0 or 1;

P is a single bond or a D or L isomer of Pro, ΔPro, Ala, MeAla, Arg, Lys, HArg, MeArg, MeLys or MeHArg;

A is a single bond, Gly, a D or L isomer of Arg, Lys, Orn, HArg, MeArg, MeLys, MeOrn, MeHArg, or Gln;

D is a single bond, Gly, or a D or L isomer of Arg, Lys, HArg, MeArg, MeLys, MeHArg, Gln or Orn;

B is OH, NH$_2$, NHAlk or NH (CH$_2$)$_m$NHR;

Z is Phe, Phe(4'—Alk), Tyr(Alk), Ile or Tyr;

X is a D or L isomer of Phe, Phe(4'—Alk), Val, Nva, Leu, Ile, Pba, Nle, Cha, Abu, Met, Chg, Tyr, Trp or Tyr(Alk);

Y is Val, Ile, Abu, Ala, Chg, Gln, Lys, Cha, Nle, Thr, Phe, Leu or Gly;

m is 2 to 6;

R is H or C(=NH)NH$_2$ and

* is to indicate D isomer, L isomer or a D,L mixture.

Subgeneric groups of compounds of this invention comprise compounds of formula I in which the P—A—D—B tail is Pro—Arg—NH$_2$, Arg—Gly—NH$_2$, Pro—Arg—Gly—NH$_2$, Arg—DArg—NH$_2$, DArg—DArg—NH$_2$, Put(G), NMeArg—Arg—NH$_2$, Pro—Arg—NH(CH$_2$)$_2$NH$_2$, Arg—NH$_2$, and Arg—Gly—Arg—NH$_2$. In formula I, n is preferably 1 and X is a D-isomer unit.

Also included in this invention are addition salts, complexes or prodrugs, such as esters of the compounds of this invention when B is OH, especially the nontoxic, pharmaceutically acceptable acid addition salts. The acid addition salts are prepared in standard manner in a suitable solvent from the parent compound and an excess of an acid, such as hydrochloric, hydrobromic, sulfuric, phosphoric, acetic, maleic, succinic, ethane disulfonic or methanesulfonic acids. Certain end products of formula I such as the Arg$^7$—Arg$^8$ compounds have two strong basic groups in their structures, therefore, their acid addition salt derivatives are easily prepared. The ester derivatives of the acid forms of the end products, such as the methyl, ethyl or benzyl esters, are prepared as known to the art.

The end products (I) of this invention are prepared by cyclization of the corresponding novel linear peptide (II):

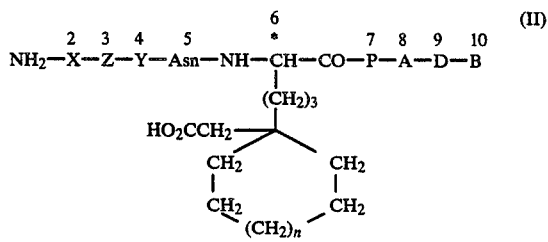

$$\begin{array}{c} \phantom{XX} \overset{6}{*} \phantom{XXXXX} \\ NH_2-\overset{2}{X}-\overset{3}{Z}-\overset{4}{Y}-\overset{5}{Asn}-NH-CH-CO-\overset{7}{P}-\overset{8}{A}-\overset{9}{D}-\overset{10}{B} \end{array} \quad (II)$$

in which X, Z, Y, P, A, D, B, n and * are as defined above with any chemically reactive centers protected as described below. Also included are any addition salt forms of compounds of Formula II as noted above for the end compounds of formula I. It should be emphasized that the linear intermediate structure II can be cyclized only in the form of the free base of X. No cyclization occurs when the salt form is present but the salt forms are important derivatives for isolation and characterization of the intermediates.

The cyclization involves the formation of an amide bond between the α-amino group of the X unit at position 2 and the free ω-carboxy group of the 6,6 substituted 2-amino suberic acid unit at position 6 of structure II. Any chemical method of amide formation is employed such as reaction using dicyclohexylcarbodiimide plus hydroxybenzotriazole or 4 dimethylaminopyridine, reaction using diphenylphosphoryl azide (DPPA) and base, 1 (3 dimethylaminopropyl) 3 ethylcarbodiimide (EDC) as the methiodide or hydrochloride; the azide derivative of the carboxylic acid; a mixed anhydride such as the benzoyl, pivaloyl or isovalero-yl containing anhydride with the suberic acid; ethoxyacetylene or N-ethyl-5-phenyl-isoxazolium-3' sulfonate. All these general synthetic methods are described in Peptide Synthesis, M. Bodanszky, John Wiley, 1976, page 191 and Table 3, pages 116–121. These coupling reactions are usually run in either agueous or organic solvents until reaction is complete. Among the preferred solvents are dimethylformamide, dimethylacetacide, methylene chloride, acetonitrile or combinations thereof. The reactions are usually carried out at room temperature and in dilute solution to minimize polymerization.

Diphenylphosphoryl azide (DPPA) is a particularly useful cyclization agent. The linear peptide (II) is treated with an excess of DPPA in dried dimethylformamide and triethylamine at room temperature until thin layer monitoring demonstrates completion of the reaction. The desired product is isolated by evaporation and purified by gel filtration and high performance liguid chromatography.

The resin supported peptide chain of the linear peptides (II) is usually built up, stepwise, proceeding from the B unit and working toward the X unit through the novel Pas or Tas unit at position 6 of the linear product Each unit is properly protected as known in the peptide art and as described below. The sequence of step-reactions is conveniently carried out in a Beckman 990B peptide synthesizer or its eguivalent without isolation of each intermediate peptide. The details of the procedure are in the working examples presented hereinafter.

The various amino acids (AA), which are consecutively added to the resin supported chain, are protected as known to the art. For example, the Boc protecting group is used for an amino group, especially at the α-position; an optionally substituted benzyl for the carboxy group of the Pas or Tas unit; tosyl for the Arg, HArg or MeArg unit; and an optionally substituted carbobenzyloxy (Z) for the Tyr, Orn or Lys units. The protective groups are, most conveniently, those which are not easily removed by using mild acid treatment, such as for removing the Boc group. Rather one should use HF, sodium liguid ammonia or, for benzyl or carbobenzyloxy groups, catalytic hydrogenation.

Often, the uncyclized, resin-supported poly peptide of Formula II is synthesized in a number of synthetic cycles to offer good supplies of oligopeptide intermediates to vary the chain as described above.

The assembled, resin-supported peptide is treated with an excess of anhydrous hydrogen fluoride with an appropriate scavenger compound, such as anisole, to give the linear peptide intermediate of formula II in good yield.

The compounds of formula I are also prepared by reacting the cyclized Pas[6] carboxylic acids or derivative thereof with a protected form of PADB in the terminal acid ester or amide form and likewise the cyclized Pro[7] with protected ADB, cyclized Arg7 with protected DB or cyclized Arg[8] with B, in each case employing reaction conditions and intermediates of standard peptide methods of synthesis. Such starting material acids, such as those of formula I in which P is an arginine-like unit as defined above and A is hydroxy, are prepared as described above by either a resin-supported or a solution reaction sequence.

The key to the synthesis of the compounds of formula I and the discovery of their biological activity was the availability of the 6,6 spirocycloalkylene 2-aminosuberic acid which must be available for use in the peptide synthesis of the intermediates of formula II discussed above. 2 Amino and 2,7-diaminosuberic acids had been prepared earlier using a Kolbe electrolysis as the key step of the synthesis, R. Nutt et al., J. Org. Chem. 45 3078 (1980). The presence of the bulky spirocyclo alkylene substituent at the 6,6 position of the desired 2-aminosuberic acid made the preparation of these intermediates and the cyclization of the linear peptides of formula II unpredictable prior to the present invention.

The synthetic preparation of 6,6 spirocyclo alkylene 2-aminosuberic acids as well as the corresponding 7,7 substituted azelaic and 5,5 substituted pimelic acids involves (1) the insertion of a terminally unsaturated hydrocarbon chain at the spiro carbon of a cycloalkane carboxylate, (2) homologating the carboxylate, (3) functionalizing the unsaturated center of the side chain and (4) preparation of the amino acid therefrom. Details of the preparation are presented in Example 1.

The spirocycloalkylene 2 aminoalkandioic acid intermediates are represented by the following formula (III):

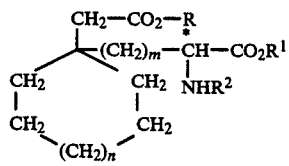

in which:
  m is 2–4;
  n is 0 or 1;
  R and $R^1$ are, each, hydrogen or a carboxy protecting group; and
  $R^2$ is hydrogen or an amino protecting group.
  * is to indicate D isomer, L isomer or a D, L mixture Carboxy protecting groups, which are useful at R or $R^1$ of formula III, are well known in the peptide art, Peptide Synthesis, loc. cit. 49–57. Representative groups are lower alkyl of 1–8 carbons, benzyls, benz hydryls, phenyls all which form ester derivatives but which are easily removed by methods known to the art. Preferably, selective removal methods must be available after the linear peptide of formula II has been prepared.

Amino protective groups, which are useful in formula III at $R^2$ are also well known, Peptide Synthesis, loc. cit. 18–48. Particularly useful are carbobenzoxy, t-butyloxycarbonyl, p-toluene sulfonyl, trifluoroacetyl, arylsulfenyl or formyl groups.

Also included in formula III are the optically active isomers. These are separated from isomeric mixtures into optically pure D- and L-isomeric form by fractional crystallization of salts with chiral bases. They can also be obtained using the novel Kolbe method of synthesis described below.

Another aspect of the invention is the chiral synthesis of these 6,6 spirocycloalkylene 2 amino alkanedioic acids. It was unexpectedly found that the bulky cycloalkylene group did not prevent formation of the desired compounds by the Kolbe electrolysis procedure. For example, 1,1 cyclohexanediacetic acid monobenzylester was electrolyzed under Kolbe conditions with N α-Boc-L-glutamic acid α-benzyl ester to give the pure L-isomer benzyl 2-L Boc amino-5 (1 carbobenzoxymethylcyclohexyl) pentanoate which is dibenzyl ester of 6,6-cyclopentamethylene 2 L Boc aminosuberic acid. The synthetic procedure to prepare these optically pure intermediates of formula III permits the preparation of the optically pure isomers of Formula I and Formula II compounds at the * position. Details of this procedure which gives optically pure products are given in Example 17.

The end compounds (Formula I) of the invention have vasopressin antagonist activity. Vasopressin is known to contribute to the anti diuretic mechanism of action within the kidney. When the action of these compounds antagonizes that of the natural anti-diuretic hormone (ADH), the body excretes water due to an increased permeability of the terminal portions of the renal tubule. The mechanism of action is at the vasopressin receptors ($V_2$ receptors) located on the plasma membrane of certain renal epithelial cells. The most notable pharmacodynamic effect of the ADH antagonists of the invention is that of a water diuretic rather than of a natriuretic such as hydrochlorothiazide.

Any patient suffering from the syndrome of inappropriate antidiuretic hormone secretion (SIADH) or from an undesirable edematous condition is a target for the claimed compounds. Examples of clinical conditions indicated for the compounds of this invention include hypertension, hepatic cirrhosis, hyponatremia, congestive heart failure or a component of any traumatic condition resulting from serious injury or disease.

The second group of vasopressin receptor sites are the vascular pressor sites ($V_1$-receptors) within the cardiovascular system itself. These are also somewhat antagonized by the compounds of this invention thereby inducing antipressor or hypotensive activity.

The compounds of this invention are also oxytocine antagonists and as such are useful to prevent premature labor and in the treatment of primary dysmenorrhea.

The compounds of this invention, therefore, are used especially to induce anti-hypertensive or diuretic activity in patients in need of such treatment. This comprises the administration internally, parenterally, buccally or by insufflation, of a nontoxic but effective quantity of the chosen compound, preferably dispersed in a pharmaceutical carrier. Dosage units of the active ingredient are selected from the range of 0.01 to 10 mg/kg, preferably 0.1 to 1 mg/kg, of base based on a 70 kg patient. The dosage units are administered to the human or animal patient from 1 to 5 times daily.

The novel pharmaceutical compositions of this invention, which contains an active antagonist ingredient of formula I, comprises a dosage unit which is dissolved or suspended in a standard liguid carrier, such as isotonic saline, and is contained in an ampoule or a multiple dose vial suitable for a parenteral injection such as for intravenous, subcutaneous or intramuscular administration. A composition for insufflation may be similar but is usually administered in a metered dose applicator or inhaler. Pulverized powder compositions may, also, be used along with oily preparation, gels, buffers for isotonic preparations, buccal losenges, trans dermal patches and emulsions or aerosols.

Antagonistic activity toward the natural anti diuretic hormone (anti-ADH activity) is determined, in vitro, in the medullary tissue of hog or human kidneys and, in vivo, in the hydropenic rat. The in vitro assay procedures for vasopressin stimulated adenylate cyclase activation or vasopressin binding activity are described by F. Stassen et al., J. Pharmacology and Experimental Therapeutics, 223, 50–54 (1982).

In the test procedure for assay of adenylate cyclase activity, the amount of $^{32}P$/cAMP formed in the absence of medullary membrane is determined (blank) The blank value is subtracted from all experimental data. The compound is tested for its effect on basal adenylate cyclase activity and/or on vasopressin stimulated activity. Each determination is carried out in triplicate. The Ka value is derived from a Lineweaver Burke plot. Rel. $V_{max} = (V_{max}\text{drug}/V_{max} \text{ vasopressin}) \times 100$. $K_i = I/[Ka'/Ka) - 1]$ where I is the concentration of the antagonist and $Ka'$ and $Ka$ are the concentrations of vasopressin reguired to give half maximal activity of adenylate cyclase in the presence and absence of antagonist, respectively.

In the test procedure for binding assays, the amount of $^3H$-vasopressin bound in the absence and in the presence of an excess of vasopressin ($7.3 \times 10^{-6}M$) is measured in triplicate. These values represent total and non-specific binding, respectively. The $K_B$ of a compound is derived from the equation for competitive inhibition: $K_B = IC_{50}/(1 + L/K_D)$, where $IC_{50}$ is the concentration reguired for 50% inhibition of $^3H$-vasopressin ($K_D$=3.6×10$^{-9}$M; 1SD=0.4×10$^{-9}$M). This is the average $K_D$ value determined on 3 preparations of hog kidney membranes.

The assay for anti-ADH activity in vivo is the hydropenic rat protocol described below:

Hydropenic Rat Screen

Food and water are removed from male rats approximately 18 hours prior to testing. Animals are housed 4 per metabolism cage. At 0 hour, the test compound is administered intraperitoneally to the test group and an equivalent volume of vehicle is administered to both control groups (fasted and non-fasted). Urine volume and osmolality are measured every hour for 4 hours. Test values are recorded as ml of urine excreted (cumulative), mEg/rat electrolyte excreted, mg/rat urea excreted, and osmolality in milli-Osmoles/kg H$_2$O. A tolerance test is used to determine significance. ED$_{300}$ is defined as the dose of compound (μg/kg) reguired to lower urine osmolality to 300 m-Osmoles/kg.

TABLE I

| COMPOUND | Swine | | Rat |
|---|---|---|---|
| | $K_B$(M) | $K_i$(M) | ED$_{300}$ (μ/Kg) |
| A | 1.2 × 10$^{-8}$ | 4.5 × 10$^{-9}$ | 9.2 |
| B | 1.7 × 10$^{-7}$ | — | 73.6 |
| C | 8.2 × 10$^{-9}$ | 4.3 × 10$^{-9}$ | 8.9 |
| D | 7.2 × 10$^{-8}$ | — | 30.8 |
| E | 1.6 × 10$^{-9}$ | — | — |

A. [1-(β-mercapto-β,β-cyclopentamethylenepropionic acid)-2-(O—ethyl-D-tyrosine)-4-valine-8-arginine-9-desglycine]vasopressin.
B. [1-(β-mercapto-β,β-cyclopentamethylenepropionic acid)-2-(O—ethyl-D-tyrosine)-4-valine-6-D-cysteine-8-arginine-9-desglycine]vasopressin.
C. [1,6-(6,6-cyclopentamethylene-2-amino-L-suberic acid)-2-(O—ethyl-D-tyrosine)-4-valine-9-desglycine]-vasopressin.
D. [1,6-(6,6-cyclopentamethylene-2-amino-D-suberic acid)-2-(O—ethyl-D-tyrosine)-4-valine-9-desglycine]-vasopressin.
E. [1,6-(6,6-cyclopentamethylene-2-amino-D,L-suberic acid)-2-(O—ethyl-D-tyrosine)-4-valine-7-arginine-8-D-arginine-9-desglycine]vasopressin.

The stereochemistry of the PAS unit in compounds C and D is assigned based on the biological activities of the two compounds as well as by amino acid analysis using chiral gas chromatographic analysis with the optically active PAS obtained from the Kolbe method as the standard. The representative data of Table I demonstrate that the Pas[1,6] compounds possess equivalent or substantially greater biological activity than their respective dithia compounds of the prior art.

The following examples are intended to demonstrate the preparation and use of this invention. All temperatures are in degrees Centigrade. Terms and symbols are those common in the chemical and peptide arts.

EXAMPLE 1

Synthesis of Spirocyoloalkylene-2-aminoalkanedioic acids (A) Methyl 1-(5-Pent-1-enyl)cyclohexane carboxylate A solution of lithium diisopropylamide was prepared by adding 2.7M n-butyl lithium (hexane) (37.0 ml, 100 mmol) to a solution of diisopropylamine (15.0 ml, 109 mmol) in dry tetrahydrofuran (170 ml) at −78° under argon, then stirring the subseguent mixture at −78° for 20 minutes. Methyl cyclohexanecarboxylate (13.0 ml, 91 mmol) was added to the solution and the reaction mixture was stirred for 30 minutes at −78°. 5-Iodopent-1-ene (18 g, 91.8 mmol) was added, the reaction continued at −78° for 10 minutes and the mixture was then slowly brought to room temperature. The reaction mixture was diluted with water, acidified (pH=2) with 3N hydrochloric acid and extracted with ether. The ether extracts were washed with saturated sodium thiosulfate (agueous), dried over magnesium sulfate and evaporated at reduced pressure to give 16 g of methyl 1-(5-pent-1-enyl)cyclohexanecarboxylate ester.

(B)
1-(O-Tosyl)hydroxymethyl-1-(5-pent-1-ene)cyclohexane

The methyl ester (A) (16 g, 76.0 mmol) was added to a solution of lithium aluminum hydride (4.6 g, 120.9 mmol) in tetrahydrofuran (205 ml) at room temperature and the resulting mixture was heated at reflux for 3 hours. The reaction was cooled to 0°, treated sequentially with water (5 ml), 3N sodium hydroxide solution (5 ml) and water (15 ml) then filtered. The filtrate was dried over magnesium sulfate, filtered and evaporated to give the titled alcohol: $^1$HNMR (CDCl$_3$): 6.17–5.60 (m, 1H), 5.20–4.80 (m, 2H), 3.40 (S, 2H) and 2.43–0.80 (m, 17H).

This alcohol was dissolved in pyridine (89 ml) and treated with p toluenesulfonyl chloride (27 g, 142.5 mmol) at 0° for 4 hours. The reaction mixture was poured into water and extracted with petroleum ether, petroleum ether:ethyl ether (1:1) and ethyl ether. The combined organic extracts were washed with 0.5N HCl (agueous), saturated sodium bicarbonate (agueous) and water, dried over magnesium sulfate, filtered and evaporated to give 30.0 g of 1 (O-tosyl)hydroxymethyl 1 (5 pent-1 ene) cyclohexane: $^1$HNMR(CDCl$_3$) 7.98–7.20 (m, 4H), 6.03–5.53 (m, 1H), 5.13–4.78 (m, 2H), 3.82 (S, 2H), 2.43 (S, 3H) and 2.23–0.73 (m, 16H).

(C) 1-Cyanomethyl-1-(5-pent1-ene)cyclohexane

The tosylate (B) (30 g) was dissolved in dimethylsulfoxide (219 ml) with sodium cyanide (13.6 g, 279 mmol). The resulting mixture was heated at 150° for 18 hours. The reaction mixture was then cooled, poured onto saturated ammonium chloride (agueous) and extracted with petroleum ether. The organic extracts were dried, filtered and evaporated. Purification of the residue using flash chromatography (silica gel; 15% ethyl acetate/hexane) gave 9.9 g of 1 cyanomethyl 1-(5-pent-1-ene)cyllohexane (57% yield from methyl cyclohexanecarboxylate): $^1$HNMR (CDCl$_3$): 6.12–5.57 (m, 1H), 5.20–4.87 (m, 2H , 2.30 (S, 2H), 2.23–1.82 (m, 2H) and 1.50 (brS, 14H).

(D) 1-Cyanomethyl-1-(4-butan-1-alyl)cyclohexane

The nitrile (C) (4.9 g, 25.6 mmol) was dissolved in methanol (80 ml). The resulting solution was cooled to −78° and treated with ozone [from a Welsbach ozone generator]until residual ozone was left in solution (blue color). The crude ozonide was treated with mehyl sulfide (20 ml) at −78° and, then, slowly warmed to room temperature. After 18 hours, the solvent was removed under reduced pressure and the residue was purified by flash chromatography (silica gel, 20% ethyl acetate/hexane) to give 3.1 g (63%) of 1-cyanomethyl-1-(4-butan-1-alyl)-cyclohexane:

NMR (CDCl$_3$): 9.80 (brS, 1H), 2.63–2.38 (m, 2H), 2.33 (S, 2H) and 1.47 (brS, 14H).

(E)
2-Amino-5-[(1-carboxymethyl)cyclohexyl]pentanoic acid

The aldehyde (D) (3.1 g, 16 mmol) was dissolved in 60% agueous ethanol (30 ml), treated with sodium cyanide (860 mg, 17.6 mmol) and ammonium carbonate (4.0 g. 41.6 mmol). The resulting solution was heated at reflux for 18 hours. Excess carbonate was removed by heating the reaction mixture at 90° for 1 hour without a condenser. The remaining solvent was removed at reduced pressure. The crude product was dissolved in hot ethanol, filtered and evaporated under reduced pressure to give the crude hydantoin: MS: (M+H)+ =264. The unpurified hydantoin was suspended in water with barium hydroxide hexahydrate (12.0 g, 38 mmol) and heated in a sealed bomb at 170° for 96 hours. The reaction mixture was cooled, diluted with water and filtered. The filtrate was passed over a BioRad AG 50W-X8 ion exchange column and the desired product was eluted off the column with 1N ammonium hydroxide (agueous). Evaporation of the ammonium hydroxide eluent gave 1.1 g of the titled amino acid (E): MS: (M+H)+ =25. This compound is also trivially named 6,6 cyclopentamethylene 2 aminosuberic acid (Pas).

(F) 2-Boc-amino-5-[(1-carboxyethyl)cyclohexyl]pentanoic acid

The amino acid (E) was dissolved in 1N sodium hydroxide solution (45 ml) and tert butanol (45 ml) and the mixture was treated at room temperature with di-tert-butyldicarbonate (980 mg, 4.5 mmol) for 48 hours. The reaction mixture was washed with hexane, acidified with sodium bisulfate and extracted with ethyl acetate. The combined organic extracts were dried, filtered and evaporated to give 1.5 g of the titled compound.

(G) Methyl 2-t-Boc amino-5-[(1-carbomethoxymethyl)cyclo-hexyl]pentanoate

The Boc diacid (F) (1.5 g) was dissolved in methylene chloride and treated with excess ethereal diazomethane at 0°. After quenching the excess diazomethane with acetic acid, the solution was evaporated at reduced pressure. The crude ester was purified by flash chromatography (silica gel, 20% ethyl acetate/hexane) to give 900 mg (56%) of the titled product: $^1$HNMR (CDCl$_3$): 5.23–4.87 (m, 1H), 4.50–4.10 (m, 1H), 3.77 (S, 3H), 3.67 (S, 3H), 2.30 (S, 2H), 1.47 (S, 9H) and 1.42 (brS, 16H).

(H) 2-t-Boc-amino-5-[(1-carbomethoxymethyl)cyclohexyl]-pentanoic acid

The Boc diester (G) (1.135 g, 2.94 mmol) was dissolved in dioxane (16 ml) and the solution treated at 5° with 3.2 ml 1N NaOH (agusous). The reaction mixture was immediately warmed to room temperature and stirred for 4 hours. The reaction mixture was acidified (pH =2) with 3N hydrochloric acid, then evaporated at reduced pressure. The residue was diluted with water and extracted with ethyl acetate. The combined organic extracts were dried, filtered and evaporated. The residue was purified by flash chromatography (silica gel, 5 to 10% methanol/chloroform) to give 836 mg (77%) of titled product. MS: (M+H)+ =372; $^1$HNMR (CDCl$_3$): 8.02 (brS, 1H), 5.28–5.00 (m, 1H), 4.47–4.07 (m, 1H), 3.65 (S, 3H), 2.30 (S, 2H), 1.47 (S, 9H) and 2.00–1.23 (m, 16H).

(I) Benzyl 2-Boc-amino-5-[(1-carbobenzoxymethyl)-cyclohexyl]-pentanoate

Boc-diacid (F) (1.34 g, 3.75 mmol) in methylene chloride (30 ml) was treated with benzyl alcohol (1.94 ml, 18.75 mmol), dimethylaminopyridine (1.01 g, 8.25 mmol) and N,N'-dicyclohexylcarbodiimide (1.70 g, 8.25 mmol) at room temperature and the mixture was stirred at room temperature for 72 hours. The reaction mixture was then filtered, evaporated at reduced pressure and the residue was dissolved in ethyl acetate which was washed with 3N hydrochloric acid, dried over MgSO$_4$ and evaporated at reduced pressure. Purification of the residue by flash chromatography (silica gel, 15% ethyl acetate/hexane) gave 1.27 g (63%) of (I): $^1$HNMR (CDCl$_3$): 7.35 (S, 10H), 5.15 (d,J=2.4 Hz, 2H), 5.07 (S, 2H) 5.05–4.70 (m, 1H), 4.50–4.05 (m, 1H), 2.27 (S, 2H), 1.45 (S, 9H) and 2.00–1.03 (m, 16H).

(J) 2-Boc-amino-5-[(1-carbobenzoxymethyl)cyclohexyl]-pentanoic acid

The Boc-diester (I) (1.27 g, 2.36 mmol) was dissolved in dioxane (15 ml) and treated with 2.6 ml 1N sodium hydroxide solution at room temperature under argon for 4 hours. The reaction mixture was acidified (pH =2) with 3N hydrochloric acid and evaporated at reduced pressure. The residue was dissolved in ethyl acetate, washed with 3N hydrochloric acid, dried over MgSO$_4$ and evaporated at reduced pressure. The residue was purified by flash chromatography (silica gel, 5% methanol/chloroform) to give 1.03 g of the title product: MS: MH+ =448); $^1$HNMR (CDCl$_3$): 7.33 (S, 5H), 5.07 (S, 2H), 5.20–4.80 (m, 1H), 4.42–4.05 (m, 1H), 2.32 (S, 2H), 1.43 (S, 9H) and 2.08–1.07 (m, 16H).

(K) Methyl 2-Boc-amino-5-[(1-carboxymethyl)cyclohexyl]-pentanoate

The Boc-benzyl ester (J) (4 mmol) is dissolved in methylene chloride and treated with excess ethereal diazomethane at room temperature. The residual diazomethane is quenched with acetic acid and the solution is evaporated at reduced pressure. The crude diester is dissolved in methanol and hydrogenated over 10% palladium-on- carbon to give, after flash chromatography (silica gel), the titled compound.

(L) General

Running the above sequence of reactions with methyl cyclopentanecarboxylate gives 2-amino-5 [-(1-carboxymethyl)cyclopentyl]pentanoic acid and 2-t-Boc amino-5-[(1-carbobenzoxymethyl)cyclopentyl]pentanoic acid. Using 4 iodobut-1 ene or 6 iodohex 1 ene in place of 5 iodo pent 1 ene in the first step of the reaction sequence described in detail above gives 2-amino-4 [(1 carboxymethyl)cyclohexyl]butanoic acid, 2 amino 6 [(1 carboxymethyl)cyclohexyl]hexanoic acid as well as their N-Boc and 1-benzyl ester derivatives. One skilled in the art will recognize the latter two amino acids are the 2-aminospirocyclopentamethylene pimelic and azelaic acids.

EXAMPLE 2

Synthesis of Linear Peptide Intermediates (A) 2-D,L-Boc-amino-5-(1-carbobenzoxymethyl)-cyclo hexylpentanoylprolyl-(N-Tos)arginyl-BHA resin.

0.5 Mmoles (0.96 g) of BHA resin was swollen in 25 ml of methylene chloride in a 30 ml reaction vessel in a manual peptide synthesizer for 4 hours. It was, then, sequentially coupled with protected arginine and proline as well as 2-D,L-boc-amino-5 (1-carbobenzoxymethyl)cyclo hexylpentanoic acid using DCC and HBT or DMAP (4-dimethyl aminopyridine) as coupling reagent in mixture of dimethyl formamide and methylene chloride as solvent.

The amounts and mole ratio of each reagent used in this experiment are as follows:

| A.A. | Coupling Agent | | Catalyst | |
|---|---|---|---|---|
| Boc—Arg(Tos) | 642 mg | DCC 5 ml/0.3 M sol. | HBT | 405 mg |
| Boc—Pro | 390 mg | DCC 5 ml/0.3 M | HBT | 405 mg |
| Boc—D,L-Pas (Bzl) | 900 mg | DCC 5 ml/0.3 M | DMAP | 183 mg |

After the sequential coupling cycles, the peptide resin (A) was treated with acetic anhydride for 1 hour in order to acetylate any unreacted amino group.

(B) Boc-(O-ethyl-D-tyrosyl)-phenylalanyl-valyl-asparagyl-(OBzl)-6,6-cyclopentamethylene-2-D,L aminosuberic acid-prolyl-(N-Tos)arginyl-BHA resin The tri-unit resin (A) from above was further sequentially coupled in four cycles with Boc—Asn, Boc—Val, Boc—Phe and Boc—D—Tyr(OEt) using DCC/HBT as coupling reagents and $CH_2Cl_2$/DMF as solvent in a manual peptide synthesizer. Each coupling was monitored by a qualitative ninhydrin test in order to test for completion. Repeated coupling is carried out when the test is positive.

The amounts of reagents used are as follows:

| A.A. | DCC | HBT |
|---|---|---|
| Boc—Asn | 560 mg | 496 mg | 621 mg |
| Boc—Val | 521 mg | 8 ml/0.3 M Solution | 621 mg |
| Boc—Phe | 636 mg | 496 mg | 621 mg |
| Boc—D-Tyr (Et) | 672 mg | 496 mg | 621 mg |

The peptide resin was, then, dried in vacuo to give the titled intermediate.

(C) $H_2N$—D—Tyr(Et)—Phe—Val—Asn—D,L—Pas—Pro—$ArgNH_2$

The peptide resin (B) was treated with 20 ml of anhydrous hydrogen fluoride at 0° with 1.5 ml of anisole added as scavanger for 1 hour for the cleavage of the peptide from the resin support and concurrently the deprotection of amino and carboxy groups.

The HF was evaporated under reduced pressure at 0°. The residue was triturated with ether, which was discarded, and was thoroughly extracted with 10 ml×3 of dimethylformamide and 10 ml×3 of 30% agueous acetic acid. The extracts were combined and evaporated under reduced pressure to give an oil which was taken up in 5% agueous acetic acid and lyophilized to give 195 mg of white powder.

This crude linear peptide, $H_2N$—D—Tyr(Et)—Phe—Val—Asn—D,L—Pas—Pro—$ArgNH_2$ as the acetate salt, was shown to be a mixture of two major components in both HPLC (Ultrasphere ODS column, 50% agueous acetonitrile with 0.1% TFA) and tlc (silica/n BuOH/ethyl acetate/acetic acid/water 1:1:1:1) with traces of other components.

This crude peptide was purified by counter current distribution (CCD) in BAW (butanol/acetic acid/water) 4:1:5 in 240 transfers. Fractions were checked by tlc and appropriate fractions were pooled, evaporated under reduced pressure and lyophilized from 1% agueous acetic acid to yield:

| Fractions (I) | 28.5 mg |
|---|---|
| Fractions (II) | 110 mg |
| Fractions (III) | 35 mg |

Isocratic HPLC (Ultrasphere ODS ; 40% agueous acetonitrile with 0.1% TTFA; flow rate equal to 1.5 ml/min) showed two peaks with retention times of 5.09 and 7.80 minutes respectively. Fraction I contained predominately the 5.09 min. isomer (approximately 90%), fraction II contained an actual amount of both isomers and fraction III contained mostly the 7.80 min. isomer. FAB-Mass spectrum confirmed the presence of the desired peptide ($MH^+ = 1061$; $MH^- = 1059$) in all three fractions.

These results indicate the two peaks are the two desired D- and L-isomers of titled linear peptide intermediate (C).

EXAMPLE 3

$$\boxed{\text{D—Tyr(Et)—Phe—Val—Asn—Pas}^{1,6}\text{—Pro—ArgNH}_2}\ \text{D and L Isomers}$$

The linear peptide (C) from Example 2 (50 mg) was treated with 1N HCl in glacial acetic acid and, then, evaporated in vacuum to dryness. This was repeated three times. The residue was taken up in dried dimethylformamide and evaporated in vacuc. This was repeated three times. (This process is to convert the acetic acid salt at the amino and guanidino groups to the corresponding stronger hydrochloric acid salt in situ and, thus, eliminate the side reaction of acetylation of the α-amino group of the D—Tyr by the liberation of the acetic acid. This conversion can also be accomplished by ion exchange column chromatography with some loss of material.)

The treated residue was dissolved in 7.5 ml of dried dimethylformamide, then 12.5 ul of triethylamine was added with stirring, followed by addition of 20 μl of diphenylphosphoryl azide (DPPA). The resulted mixture was stirred under an argon atmosphere at room temperature overnight. The completion of the cyclization is monitored by isocratic HPLC or by tlc.

The reaction mixture was evaporated to dryness and redissolved in 30% acetic acid. The salt was removed by a G-15 Sephadex gel filtration column. The product was further purified and separated into D- and L-isomers by preparative HPLC in $C_{18}$ column using 45% acetonitrile in water with 0.1% trifluoroacetic acid as mobile phase to give 8.5 mg of compound C of Table 1 above containing the L-Pas and 5 mg of compound D containing the D-Pas. The chirality of the Pas was determined by comparing the derivativized hydrosylate of compound C and D to authentic L-Pas by chiral GC analysis.

Compound C:

FAB-Mass Spec (M + H)+ = 1043, (M − H)− = 1041
HPLC  single peak  retention time = 9.72 min Amino acid analysis:

| Aspartic | 1.00 | Tyrosine | 0.97 |
| Proline | 0.69 | Phenylanaline | 0.98 |
| Valine | 0.95 | Arginine | 1.10 |

Compound D:

FAB-Mass Spec (M + H)+ = 1043, (M − H)− = 1041
HPLC  single peak  retention time = 16.24 min Amino acid analysis:

| Asp | 1.00 | Tyr | 0.92 |
| Pro | 0.76 | Phe | 0.97 |
| Val | 0.77 | Arg | 1.22 |

EXAMPLE 4

D—Tyr(Et)—Phe—Val—Asn—Pas—Pro—Arg—NH2

The linear, protected Boc—D—Tyr(Et)—Phe—Val—Asn—Pas(OBzl)Pro—Arg(Tos)—BHA was prepared in the same manner as Example 2 except optically pure Boc—L—Pas(OBzl) was used in place of Boc—D,L—Pas(OBzl). The peptide was cleaved from the resin with removal of protecting groups by treatment with liguid HF 10 ml) in the presence of anisole (1 ml) at 0° for 50 minutes. After removal of the HF under vacuum, the resin was washed with ether and air dried. The resin was then extracted with 10% HOAc 120 ml), 1% HOAc (120 ml) and water (120 ml). The aqueous extracts were combined, diluted with water and lyophilized to yield 213 mg crude linear peptide. 100 mg crude linear peptide was purified by gel filtration on G-15 with 1% HOAc to yield 62 mg purified linear peptide.

62 mg purified linear peptide (58.4 μmol) was dissolved in 5 ml HOAc and 5 ml 1.7 M HCl/HOAc and evaporated to dryness. The residue was dissolved in DMF and evaporated to dryness 3 times. The residue was then dissolved in 10 ml DMF and 12.8 μl diphenylphosphoryl azide (1.1 eg) followed by 17.8 μl triethylamine (2.2 eg) were added. The reaction mixture was kept at 4° for 3 days. An additional 6.4 μl diphenylphosphoryl azide (0.5 eg) and 8.9 μl triethylamine (1.0 eg) was then added and the reaction mixture kept at 4° overnight. The reaction mixture was then evaporated to dryness and the resulting glass was triturated with ether. The crude cyclic peptide was collected by filtration and air-dried, yielding 75 mg. The crude cyclic peptide was purified by prep hplc (Hamilton PRP—1,45% acetonitrile/water/0.1% TFA). The appropriate fraction were pooled, evaporated to dryness and lyophilized from 1% HOAc to yield 35.3 mg purified cyclic peptide. FAB—MS m/z 1043.7 (MH+),HPLC k′=2.92 (45% acetonitrile/water/0.1% TFA). This compound coeluted with compound C in Example 3.

EXAMPLE 5

Procedure for Terminal Coupling

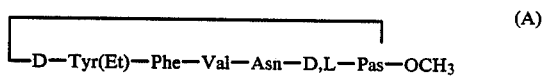
(A)
D—Tyr(Et)—Phe—Val—Asn—D,L—Pas—OCH3

The protected peptide intermediate resin, i.e., Boc—D—Tyr(Et)—Phe—Val—Asn—D,-L—Pas—OCH2C6H4—Resin—OCH3 is synthesized manually on a shaker. Boc-D,L-Pas(OCH2C6-H4—Resin)OCH3 is prepared from Boc—D,-L—Pas—OCH3 by direct coupling to hydroxymethyl resin with DMAP/DCC in CH2Cl2 with substitution of 0.50 meg./g. The protected peptide resin intermediate is synthesized stepwise by deprotecting the Boc—group using 1:1 TFA:CH2Cl2 and coupling sequentially with the appropriate Boc-amino acids using DCC/HBT as activating and catalyzing reagents on 1.0 mmol scale to give the resin coupled intermediate. The linear peptide is obtained by cleavage from the resin using HF 20 ml in the presence of 2.0 ml of anisole at −10° for 60 min. After evaporation in vacuo to dryness, the residue is washed with anhydrous diethyl ether and is extracted with TFA, degassed dimethylformamide, and acetic acid. The extracts were combined, evaporated in vacuo to drynes, taken up in acetic acid and lyophilized to give the crude linear peptide. Cyclization of this peptide, NH2—D—Tyr(Et)—Phe—Val—Asn—D,-L—Pas—OCH3 (150 mg) with DPPA (45μl) and Na2-CO3 (45 mg) in DMF (120 ml) at room temperature overnight with yields after evaporation and prep. HPLC, 80 mg cyclic peptide diasteromers not separated). FAB—MS:m/z 805 (MH+)1 m/z 803 (M—H)−; hplc:RT =26.7, 27.2 min (Ultrasphere C-18, mobile phase A: 0.1% TFA/H2O, B:0.1% TFA/CH3CN; linear gradient 70–40% A, 30 min, 40% A, 10 min).

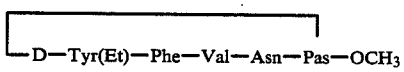
(B)
D—Tyr(Et)—Phe—Val—Asn—Pas—OCH3

Repeating the same synthesis as in (A) using Boc—L—Pas—OCH3 in place of Boc—D,-L—Pas—OCH3 yields after purification cyclo [D—Tyr—(Et)—Phe—Val—Asn—L—Pas]—OCH3.

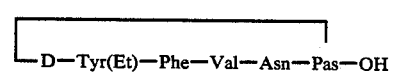
(C)
D—Tyr(Et)—Phe—Val—Asn—Pas—OH

A suspension of 0.1 mmol of the methyl ester (A) above in 1:1 dioxane −10% K2CO3 (aqueous) is stirred at room temperature for 8 hours. The reaction mixture is diluted with water and acidified to pH =4 with glacial acetic acid. The resulted solution is evaporated in vacuo and the residue purified by gel chromatography.

(D) D—Tyr(Et)—Phe—Val—Asn—Pas—NHNH₂

The methyl ether (A) above (100 mg) is treated with anhydrous hydrazine in methanol at room temperature to give after evaporation the titled compound, the hydrazide.

(E) Condensation

The 6-Pas acid (20 mg) from (C) above is reacted with one eguivalent of N—ε—BocLys—Arg(NH₂) 2HCl in the presence of DCC, HBT and one eguivalent of triethylamine in dimethylformamide followed by treatment with trifluoroacetic acid to produce cyclco[-D—Tyr(Et)—Phe—Val—Asn—Pas]—Lys—Arg—NH₂.

Similarly the corresponding 7-Arg acid cyclized peptide and the 7-Pro cyclized peptide acid congeners are made from reacting the acylazide derived from the hydrazide (D) using arginine or proline. Either acid compound is isolated as the potassium salt if desired. One eguivalent of Arg—NH₂.2HCl is coupled with the corresponding 7—D—Pro acid made as described using DCC/HBT to give the respective 7—D—Pro—Arg—NH₂ peptide.

EXAMPLE 6

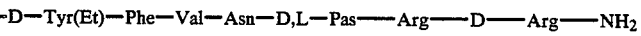
D—Tyr(Et)—Phe—Val—Asn—D,L—Pas——Arg——D——Arg——NH₂

The linear, protected peptide Boc—D—Tyr(Et)—Phe—Val—Asn—D,L—Pas(OBzl)—Arg(Tos-)—D—Arg(Tos)—BHA was prepared in the usual manner. The linear peptide was cleaved from the resin with removal or protecting groups by treatment with liguid HF 10 ml) in the presence of anisole (1 ml) at 0° for 50 minutes. After removal of the HF under vacuum, the resin was washed with ether and air-dried. The resin was then extracted with 60 ml 10% HOAc. 60 ml 1% HOAc and 60 ml water. The extracts were combined, diluted with water and lyophilized to yield 324 mg crude linear peptide. 275 mg linear peptide was purified by countercurrent distribution (nBuOH/HOAc/water 4:1:5) to yield 166.7 mg purified linear peptide.

66.7 mg linear peptide (59.6 μmol) was dissolved in 5 ml HOAc and 5 ml 1.8 M HCl/HOAc. The solution was evaporated to dryness and the residue dissolved in DMF and evaporated to dryness 3 times. The residue was then dissolved in 10 ml DMF and 12.9 μl diphenylphosphoryl azide (1N1eg) was added followed by 18 μl triethylamine (2.2 eg). The reaction mixture was kept at 4° for 3 days. An additional 6.5 μl diphenylphosphoryl azide (0.5 eg) and 9 μl triethylamine (1.0 eg) was added and the reaction kept at 4° overnight. The reaction mixture was then evaporated to dryness and the residue triturated with ether to yield the crude cyclic peptide as a slightly hygroscopic solid which was collected by filtration. The peptide was dissolved in 5 ml methanol and purified by prep HPLC on Hamilton PRP-1 (9 mm×30 cm) using 33% acetonitrile/water/0.1% TFA. The appropriate fractions were pooled, evaporated to dryness and lyophilized from 1% HOAc to yield 45.0 mg purified cyclic peptide. FAB—MS m/z 1102.8 (MH+), HPLC k′=5.0 (Hamilton PRP 1, mobile phase A 0.1% TFA, B 0.1% TFA/acetonitrile, linear gradient 20–50% B, 15 minutes, 50% B, 5 minutes).

EXAMPLE 7

D—Tyr(Et)—Phe—Val—Asn—Pas—Arg—D—Arg—NH₂

The linear, protected peptide Boc—D—Tyr(Et)—Phe—Val—Asn—Pas(OBzl)—Arg(Tos)—D—Arg(Tos)—BHA was prepared in the usual manner. 2.0 g of the peptide-resin was cleaved with removal of protecting groups by treatment with liguid HF (40 ml) in the presence of dimethylsulfide (2.0 ml) at 0° C. for 60 minutes. After removal of the HF under vacuum, the resin was washed with ether, extracted with 50% acetic acid, 20% acetic acid and water. The extracts were combined and lyophilized to yield 1.07 g crude linear peptide.

1.07 g of the crude, linear peptide (956 μmol) was purified via HPLC on Vydac ODS using 25% acetonitrile/0.1 M triethylammonium phosphate. The purified peptide was then adsorbed onto an SM-2 column, washed with 0.05M HCl, and eluted from the column with 90% MeOH to yield 358 mg of linear peptide as the hydrochloride salt.

125 mg of linear peptide (108 μmol) was then dissolved in 21 ml DMF. 36.2 μl of triethylamine (259 μmol) was added followed by 28.0 μl of diphenylphosphoryl azide (130 μl ). The solution was kept at 4° for three days. The reaction mixture was then evaporated to dryness and the residue triturated with ether. The crude cyclic peptide was then purified via HPLC (Hamilton PRP-1, 33% acetonitrile/water/0.1% TFA) to yield, after lyophilization from 1 M HOAc, 90 mg of cyclic peptide. FAB—MS m/z 1102 (MH+), HPLC k′=4.5 (IBM ODS, mobile phase A=0.1 M triethylammonium phosphate, B=acetonitrile, linear gradient 30–40% B, 10 minutes, 40–60% B, 20 minutes).

EXAMPLE 8

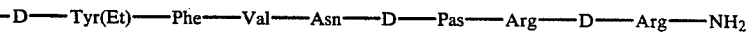
D——Tyr(Et)——Phe——Val——Asn——D——Pas——Arg——D——Arg——NH₂

The linear, protected peptide Boc—D—Tyr(Et)—Phe—Val—Asn—D—Pas(OBzl)—Arg(Tos-)—D—Arg(Tos)—BHA was prepared in the usual manner. The linear peptide was cleaved from the resin with removal of protecting groups by treatment with liguid HF (10 ml) in the presence of anisole (1 ml) at 0° for 50 minutes. After removal of the HF under vacuum, the resin was washed with ether and air dried. The resin was then extracted with 60 ml 10% HOAc, 60 ml 1% HOAc and 60 ml water. The extracts were combined, diluted with water and lyophilized to yield 335 mg crude linear peptide. The crude linear peptide was purified by countercurrent distribution (nBuOH/HOAc/water 4:1:5) to yield 287.9 mg partially purified linear peptide. 100 mg of the partially purified peptide was further purified by gel filtration on G-15 using 10% HOAc to yield 38 mg purified linear peptide.

38 mg linear peptide (33.9 μmol) was dissolved in 5 ml HOAc and 5 ml 1.8 M HCl/HOAc. The solution was evaporated to dryness and the residue dissolved in DMF and evaporated to dryness 3 times. The residue was then dissolved in 6 ml DMF and 7.4 μl diphenylphosphoryl azide (1.1 eq) was added followed by 10.4 μl triethylamine (2.2 eq). The reaction mixture was kept at 4° for 3 days. An additional 3.7 μl diphenylphosphoryl azide (0.5 eq) and 5.2 μl triethylamine (1.0 eq) was added and the reaction kept at 4° overnight. The reaction mixture was then evaporated to dryness and the residue triturated with ether to yield the crude cyclic peptide as a slightly hydroscopic solid which was collected by filtration. The peptide was dissolved in 2 ml methanol and purified by prep HPLC on Hamilton PRP—1 (9 mm×30 cm) using 35% acetonitrile/water/0.1% TFA. The appropriate fractions were pooled, evaporated to dryness and lyophilized from 1% HOAc to yield 25.6 mg purified cyclic peptide. HPLC k′=5.0 (Hamilton PRP—1, mobile phase A 0.1% TFA, B 0.1% TFA/acetonitrile, linear gradient 20–50% B, 15 minutes, 50% B, 5 minutes).

EXAMPLE 9

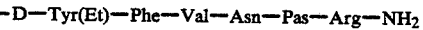

The linear, protected peptide Boc—D—Tyr(Et)—Phe—Val—Asn—Pas(OBzl)—Arg(Tcs)—BHA was prepared in the usual manner. The linear peptide was cleaved from the resin with removal of protecting groups by treatment with liguid HF(10 ml) in the presence of anisole (1 ml) at 0° for 50 minutes. After removal of the HF under vacuum, the resin was washed with ether and air dried. The resin was then extracted with 30 ml 50% HOAc, 60 ml 10% HOAc, 60 ml 1% HOAc and 60 ml water. The extracts were combined, diluted with water and lyophilized to yield 564 mg crude linear peptide. The resin gas re-extracted with DMF, which was evaporated to dryness and the residue lyophilized from 10% HOAc to yield an additional 113 mg crude linear peptide.

100 mg crude, linear peptide (103.7 μmol) was dissolved in 10 ml HOAc and 2 ml DMF. To this was added 10 ml of 1.8 M HCl/HOAc. The solution was evaporated to dryness and the residue dissolved in DMF and evaporated to dryness 3 times. The residue was then dissolved in 20 ml DMF and 22.5 μl diphenylphosphoryl azide (1.1 eq) was added followed by 31.7 μl triethylamine (2.2 eq). The solution was kept at 4 for three daysN An additional 10 μl diphenylphosphoyl azide (0.5 eq) and 7.2 μl triethylamine (0.5 eq) was added and the reaction kept at 4° overnight. The reaction mixture was then evaporated to dryness and the residue was triturated with ether to yield a yellow, slightly hygroscopic solid which was collected by filtration. The crude cyclic peptide was purified by countercurrent distribution (nBuOH/EtOAc/HOAc/water 2:2:1:5) followed by gel filtration (G—15, 10% HOAc) to yield 32.6 mg purified cyclic peptide. FAB—MS m/z 946 (MH+), HPLC k′=4.95 (Hamilton PRP—1, mobile phas A=0.1% TFA, B=0.1% TFA/acetonitrile, linear gradient 20–50% B, 15 minutes, 50% B 5 minutes.

EXAMPLE 10

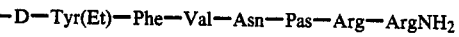

The protected peptide intermediate resin, D—Tyr(Et)—Phe—Val—Asn—Pas(OBzl)—Arg(Tos)—Arg(Tos)—BHA is synthesized on 1.0 mmol of benzhydrylamine resin as above. The HF cleavage and cyclization with DPPA are performed as described to give the partially purified crude peptide.

EXAMPLE 11

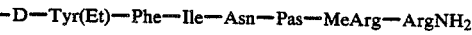

The protected peptide intermediate resin, Boc—D—Tyr(ET)—Phe—Val—Asn—Pas(OBzl)—N—MeArg(Tos)—Arg(Tos)—BHA is prepared by the solid-phase method on benzhydrylamine resin on a shaker using 0.5 mmol of BHA resin is used. All amino acids are protected as tert.-butyloxycarbonyl on the nitrogen and coupled sequentially using DCC/HBT, while the Pas(Bzl) is coupled using DMAP. The peptide is cleaved from the resin with deprotection of the side-chain protecting groups using anhydrous HF (20 ml) and anisole (2 ml) at 0° for 60 minutes. The peptide is extracted from the resin with aqueous HOAc/DMF. After evaporation in vacuo to dryness, the peptide residue is washed with anhydrous diethyl ether and cyclized as described with DPPA to give the titled compound.

EXAMPLE 12

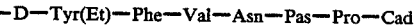

To a solution of the Pro[7]—acid, prepared as described in Example 5, (0.033 mmol) and mono—Boc—1,5—diaminopentane (20.2 mg, 0.0996 mmol) in dimethylformamide (400 ul , dicyclohexylcarbodiimide (10.3 mg, 0.05 mmol) and 1-hydroxybenzotriazole hydrate (13.4 ml, 0.1 mmol) are added. The reaction mixture is stirred at room temperature for 19 hours. The dimethylformamide is then removed under vacuum. The residue is treated with trifluoroacetic acid at 0° for 2 hours. After this time, the trifluoroacetic acid is removed under vacuum and the residue in 1% acetic acid is passed over a BioRex 70 (H+) ion exchange column. The basic products are washed off the ion exchange column with pyridine buffer (H$_2$O/pyridine/HOAc, 66:30:4) and evaporated. Final purification by preparative HPLC (5u Ultrasphere ODS) gives the title compound as the base or the acetate salt.

EXAMPLE 13

(A)

Boc—D—Tyr(Et)—Phe(4′—Et)—Val—Asn—Pas(Bzl)—Pro—Arg—(Tos)—Gly—BHA—resin.

Boc—Val—Asn—Pas(Bzl)—Pro—Arg(Tos)—Gly—BHA resin (3 mmol) is prepared as described above. Further coupling sequentially 1 mmole of this peptide resin with Boc—Phe—(4′—Et) and Boc—D—Tyr(Et) using 3 mmoles of amino acid and 3 mmoles of DCC and 6 mmoles of 1 hydroxybenzotriazole as catalyst. The final peptide resin is washed with methylene chloride and vacuum dried to give the titled product.

(B)

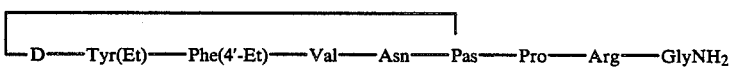

1.55 Grams of Boc—D—Tyr(Et)—Phe(4′—Et)—Val—Asn—Pas(Bzl)—Pro—Arg(Tos)—Gly—B-HA—resin from A is treated with hydrogen fluoride and subsequent cyclization with an excess of DPPA as described above to give the titled compound.

EXAMPLE 14

Using the methods of synthesis described in detail above, the following specific compounds are produced.

A. [1,6-(6,6-cyclopentamethylene-2-aminosuberic acid)-2-(O-ethyl-D-tyrosine)-4-valine-7-desproline-8-arginine]vasopressin;

B. [1,6-(6,6-cyclopentamethylene-2-aminosuberic acid)-2-D-valine-3-(O-ethyltyrosine)-4-valine-8-arginine]-vasopressin.

C. [1,6-(6,6-cyclopentamethylene-2-aminosuberic acid)-2-D-cyclohexylalanine-7-desproline-8-arginine]-vasopressin.

D. [1,6-(6,6-cyclopentamethylene-2-aminosuberic acid)-2-methionine-4-alanine-7-D-(N-methylalanine)-8-arginine-9-desglycine]vasopressin.

E. [1,6-(6,6-cyclopentamethylene-2-aminosuberic acid)-2-(O-ethyl-D-tyrosine)-4-valine-7-desproline-8-arginine 9-desglycine]vasopressin.

F. [1,6-(6,6-cyclotetramethylene-2-aminosuberic acid)-2-norleucine-3-isoleucine-4-cyclohexylglycine-8-arginine]vasopressin.

G. [1,6-(6,6-cyclopentamethylene-2-aminosuberic acid)-2-(O-methyltyrosine)-4-valine-7-desproline-8,9-bishomoarginine]vasopressin.

H. [1,6-(6,6-cyclopentamethylene-2-aminosuberic acid-2-(O-ethyl-D-tyrosine)-4-valine-7-desproline-8-arginine]vasopressin;

I. [1,6-(6,6-cyclopentamethylene-2-aminosuberic acid)-2-L-tyrosine)-4-valine-8,9-bisarginine]vasopressin.

EXAMPLE 15

Using the methods of synthesis described in detail above, the following specific compounds are produced.

A. 1,6-(6,6-cyclopentamethlene-2-amino-D-suberic acid)-2-(O-ethyl-D-tyrosine)-4-valine-7-desproline 8-arginine]vasopressin.

B. [1,6-(6,6-cyclopentamethylene-2-amino-L-suberic acid)-2-(O-ethyl-D-tyrosine)-4-valine-8-arginine]-vasopressin.

C. [1,6-(6,6-cyclopentamethylene-2-amino-D-suberic acid)-2-(O-ethyl-D-tyrosine-4-valine-8-arginine]-vasopressin.

D. [1,6-(6,6-cyclopentamethylene-2-amino-L-suberic acid)-2-D-tyrosine-4-valine-7-arginine-8-D-arginine-9-desglycine]vasopressin.

E. [1,6-(6,6-cyclopentamethylene-2-amino-D-suberic acid)-2-D-tyrosine-4-valine-7-arginine-8-D-arginine-9-desglycine]vasopressin.

F. [1,6-(6,6-cyclopentamethyline-2-amino-L-suberic acid)-2-D-phenylalanine-4-valine-7-arginine-8-D-arginine-9-desglyine]vasopressin.

G. [1,6-(6,6-cyclopentamethylene-2-amino-D-suberic acid)-2-D-phenylalanine-4-valine-7-arginine-8-D-arginine-9-desglycine]vasopressin.

H. [1,6-(6,6-cyclopentamethylene-2-amino-L-suberic acid)-2-(O-ethyl-D-tyrosine)-4-valine-7-D-arginine-8-D-arginine-9-desglycine]vasopressin.

I. 1,6-(6,6-cyclopentamethylene-2-amino D-suberic acid)-2-(O-ethyl-D-tyrosine)-4-valine-7-D-arginine-8-D-arginine-9-desglycine]vasopressin.

J. [1,6-(6,6-cyclopentamethlene-2-amino-D-suberic-acid)-2-(O-ethyl-D-tyrosine)-4-valine-7-N-methyl-arginine-8-arginine-9-desglycine]vasopressin.

K. [1,6-(6,6-cyclopentamethylene-2-amino-D-suberic acid)-2-(O-ethyl-D-tyrosine)-4-valine-7-desproline-8-(1-amino-4-guanidinobutane)-9-deslycinamide]-vasopressin.

L. [1,6-(cyclopentamethylene-2-amino-D-suberic acid)-2-(O-ethyl-D-tyrosine)-4-valine-7-desproline 8-arginine-9-desglycine]vasopressin.

M. [1,6-(6,6-cyclopentamethylene-2-amino-D-suberic acid)-2-(O-ethyl-D-tyrosine)-4-valine-8-arginine-9-diaminoethane]vasopressin.

N. [1,6-(6.6-cyclopentamethylene-2-amino-D-suberic acid)-2-(O-ethyl-D-tyrosine)-4-valine-7-desproline-8-arginine-9-(1-amino-4-guanidinobutane)]vasopressin.

O. [1,6-(6,6-cyclopentamethylene-2-amino-L-suberic acid)-2-(O-ethyl-D-tyrosine)-4-valine-7-arginine-8-glycine-9-arginine]vasopressin.

P. [1,6-(6,6-cyclopentamethyene-2-amino-D-suberic acid)-2-(O-ethyl-D-tyrosine)-4-valine-7-arginine-8-glycine 9-arginine]vaspressin.

Q. [1,6-(6,6-cyclopentamethylene-2-amino-D-suberic acid)-2-(O-ethyl-D-tyrosine)-4-valine-8-glutamine-9-arginine]vasopressin.

EXAMPLE 16

Parenteral Dosage Unit Compositions

A preparation which contains 0.1 mg of a peptide of Example 3 as a sterile dry powder for parenteral injection is prepared as follows: 0.5 mg of peptide is dissolved in 1 ml of an agueous solution of 20 mg of mannitol. The solution is filtered under sterile conditions into a 2 ml ampoule and lyophilized. The reconstituted solution is administered to a patient in need of vasopressin V₂-antagonist treatment as necessary, from 1–5 times daily by injection, or in an equivalent continuous i.v. drip injection.

Nasal Dosage Unit Compositions 2.5 Mg of a finely ground peptide of this invention, such as a product of Example 3, is suspended in a mixture of 75 mg of benzyl alcohol and 1.395 g of a suspending agent such as a commercial mixture of semisynthetic glycerides of higher fatty acids. The suspension is placed in an aerosol 10 ml container which is closed with a metering valve and charged with aerosol propellants. The contents comprise 100 unit doses which are administered intranasally to a subject in need of aquaretic therapy from 1–6 times a day.

EXAMPLE 17

Synthesis of Optically Pure Formula III Compounds (A) Synthesis of optically pure benzyl 2-L-Boc-amino-5-[(1-carbobenzoxymethyl)cyclohexyl-pentanoate (1) 1,1-Cyclohexanediacetic Anhydride Acetyl chloride (35 ml 492 mmol) was added to 1,1 cyclohexanediacetic acid (25 g, 125 mmol) in a round bottom flask and the suspension was heated for 3 hrs. at 60° C. using an oil bath. After about 15 min. the suspension became clear. The reaction was attached to a short path condenser and was heated to 100° C. under vacuum to remove volatile by-products. $^1$HNMR indicated no starting diacid and GC indicated >99% purity. Upon cooling to room temperature the anhydride solidified. $^1$H-NMR (CDCl$_3$): δ2.65(s,4H); 1.45(m,10H)

(2) 1,1 Cyclohexanediacetic Acid Mono-benzyl ester

Toluene (25 ml), benzyl alcohol (14.2 ml 137 mmol) and pyridine (10.1 ml, 125 mmol) were added to the 1,1-cyclohexanediacetic anhydride from above and the resulting solution was stirred at 100° C. overnight. The reaction was taken into ethyl acetate, washed with 1N HCl(aqueous) and saturated NaCl solution (aqueous), dried over MgSO$_4$, filtered and then evaporated to give a thick oil (37.99 g). Gas chromatography indicated 92.2% purity with the major impurity being benzyl alcohol. $^1$H-NMR (CDCl$_3$): δ11.0(s,1H); 7.25(s,5H); 5.0(s,2H); 2.5(s,2H); 1.4(br s,10H)

(3) Benzyl 2-L-Boc-amino-5-[(1-carbobenzoxymethyl)cyclohexyl]pentanoate

Sodium (0.15g) was added to a large metal beaker containing methanol (200 ml) followed by pyridine (80 ml), 1,1-cyclohexanediacetic acid monobenzyl ester (35 g) and N-α-Boc-L-Glu-α-benzyl ester (25 g,74 mmol) dissolved in methanol(40 ml). The solution was electrolized with vigorous mechanical stirring at 100 volts and 2.5 amps between two platinum plates (25×50 mm) spaced 2 mm apart. The temperature of the reaction was kept between 20°-25° C. by the aid of an isopropanol/dry ice bath. After 9 hr, TLC indicated most of the starting Boc-amino acid was reacted. The reaction was evaporated to give a brown oil which was taken into 1:1 ethyl acetate: n-hexane. The precipitate was filtered off and the filtate was washed two times with dilute HCl (aqueous), two times with 1N Na$_2$CO$_3$ (aqueous), once with sat.NaCl (aqueous), dried over MgSO$_4$, filtered and evaporated to give an oil. The majority of the impurities were removed by flash chromatography (silica gel, 5-10% ethyl acetate:n-hexane). Final purification was achieved using a 3.0×100cm silica gel column eluted with 7% ethyl acetate:n-hexane. A pure fraction contained 7.17 g, 18% of the desired product. This material was identical to the authentic D,L material(I) except that it was optically active. [α]$_D$=−14.7 c=0.1025 in methanol.

(B) 2-L-Boc-amino-4-[(1-carbobenzoxymethylcyclohexyl]-butanoic acid (1) Benzyl 2-L-Boc-amino4-[(1-carbobenzoxymethyl)-cyclohexyl])butanoate.

Sodium (0.15 g) was added to large metal beaker containing methanol (200 ml) followed by pyridine (80 ml), 1,1-cyclohexanediacetic acid monobenzyl ester (35 g) and N-α-Boc-L-Asp-α-benzyl ester (25 g,77 mmol) dissolved in methanol(40 ml). The solution was electrolized with vigorous mechanical stirring at 100 volts and 2.5 amps between two platinum plates (25×50 mm) spaced 2 mm apart. The temperature of the reaction was kept between 20°-25° C. by the aid of an isopropanol/dry ice bath. After 9 hr, TLC indicated most of the starting Boc-amino acid was reacted. The reaction was evaporated to give a brown oil which was taken into 1:1 ethyl acetate: n-hexane. The precipitate was filtered off and the filtate was washed two times with dilute HCl (aqueous), two times with 1N Na$_2$CO$_3$ (aqueous), once with sat.NaCl (aqueous), dried over MgSO$_4$, filtered and evaporated to give an oil. The majority of the impurities were removed by flash chromatography (silica gel, 5-10% ethyl acetate:n-hexane). Final purification was achieved using a 3.0×100 cm silica gel column eluted with 7% ethyl acetate:n-hexane. A pure fraction containing 6.03 g, 15% of the desired product. $^1$H-NMR (CDCl$_3$): δ7.35(s,10H; 5.3-5.0(m,3H); 5.1(s,2H); 4.3(br m,1H); 2.3(s,2H); 1.9-1.0(m,14H); 1 45(s,9H)

(2) 2-L-Boc-amino-4-[(1-carbobenzoxymethyl)cyclohexyl]butanoic acid.

NaOH (aqueous) (1N,16 ml) was slowly added to benzyl 2-L-Boc-amino-4-(1-carbobenzyoxymethyl)cyclohexyl]butanoate (6.5g, 12mmol) in dioxane (32ml) with stirring at room temperature. After stirring overnight the reaction was taken up in water acidified with 1N HCl then extracted two times with ethyl acetate. The ethyl acetate phases were combined, washed with sat.NaCl (aqueous), dried over MgSO$_4$, filtered, and evaporated to give an ozil. The product was purified on a silica gel column (3×100 cm) eluted with chlorcform, methanol, acetic acid (99:1:0.1). A pure fraction was obtained weighing 3.03 g, 56%. $^1$H-NMR (CDCl$_3$): δ7.05(s,5H); 5.1(br d,1H); 4.9(s,2H); 4.1 (br m,1H); 2.2(d,2H); 2.0-1.1(m,14H); 1.5(s,9H) Mass spectrum (M=H)$^+$=434

(C) 2 L-Boc-amino-6-[(1-carbobenzoxymethyl) cyclohexyl]hexanoic acid (1) Synthesis of 1 carbobenzoxymethyl 1 carboxyethylcyclohexane.

Oxalyl chloride (40ml) was added to 1,1-cyclohexanediacetic acid monobenzylester (50 g, 172mmol) in toluene (200 ml) with stirring at room temperature (vigorous gas evolution). After two hours the solution was evaporated to an oil then re-evaporated two times with toluene. Drying under vacuum left the acid chloride (54 g, guantitative) as a slightly yellowish oil. $^1$H-NMR (CDCl$_3$): δ7.0(s,5H); 4.9(s,2H); 3.0(s,2H); 2.4(s,2H); 1.35(br s,10H)

The acid chloride above (13.5g) in ethyl ether (25ml) was added dropwise to diazomethane (from 34.5 g Diazald ®) in ethyl ether (350 ml) with stirring in a ice bath. Gas evolution could be seen. After stirring for three hours the excess diazomethane was destroyed by the slow addition of acetic acid (2.5ml) and the reaction evaporated to dryness. The above reaction was repeated four times to give, after flash column purification (silica gel eluted with 7.5% ethyl acetate in n-hexane), the diazomethylketone. (45.5 g, 84%) $^1$H-NMR (CDCl$_3$): δ7.0(s,5H); 5.1(s,1H); 4.9(s,2H); 2.45(s,2H); 2.35(s,2H); 1.4(br s,10H)

To the diazomethylketone above (45.5g) in methanol was added dropwise silver benzoate (3.1 g) in triethylamine (385 ml) with stirring at 0° C. The reaction was shielded from light with aluminum foil and stirred for three hours at room temperature. After de-colorizing with charcoal the reaction was filtered then evaporated to a brown oil. The oil was taken up in ethyl acetate and washed with 1N HCl, saturated NaCl (agueous), dried over MgSO4, filtered then evaporated. The crude product was flashed chromatographed on silica gel eluting with 2.5% ethyl acetate in n-hexnne to give 1-carbobenzoxymethyl-1-carbomethoxyethylcyclohexane. (40.4g, 74%) $^1$H-NMR (CDCl3): δ7.0(s,5H); 4.9(s,2H); 3.45(s,3H); 2.35–2.1(m,2H); 2.2(s,2H); 1.8–1.55(m,2H); 1.35(br s,10H)

To the above 1-carbobenzoxymethyl-1-carbomethoxyethylcyclohexane (40.4g) in dioxane (300ml) was added 1N NaOH (150 ml) dropwise over 2 hours with stirring at room temperature. After 6 hours the reaction was neutralized with 1N HCl then the dioxane was evaporated. The cloudy solution was diluted with water, acidified with 1N HCl, then extracted two times with ethyl acetate, washed with saturated NaCl (agueous), dried with MgSO4, filtered and then concentrated to an oil. By $^1$H-NMR no mono-methyl ester could be seen in the crude reaction mixture, the major by-product being the di-acid. The product was purified by flash chromatography (silica gel, eluted with CHCl3, MeOH,HOAc 99:1:0.1) then distilled free of the residual benzyl alcohol to give 1-carbobenzoxymethyl-1-carboxyethylcyclohexane. (29.6 g, 76%) $^1$H-NMR (CDCl3) δ7.05(s,5H); 4.9(s,2H); 2.35–2.1(m,2H); 2.2(s,2H); 1.85–1.55(m,2H); 1.35(br s,10H)

(2) Benzyl 2-L-Boc-amino-6-(1-carbobenzoxymethyl)-cyclohexylhexanoate

Sodium (0.15 g) was added to a large metal beaker containing methanol (200 ml) followed by pyridine (80 ml), 1-carbobenzoxymethyl-1-carboxyethylcyclohexane (25 g) and N-α-Boc-L-Glu-α-benzyl ester (25 g, 74 mmol) dissolved in methanol (40 ml). The solution was electrolized with vigorous mechanical stirring at 100 volts and 2.5 amps between two platinum plates (25×50 mm) spaced 2 mm apart. The temperature of the reaction was kept between 20°–25° C. by the aid of an isopropanol/dry ice bath. After 9 hr, TLC indicated most of the starting Boc amino acid was reacted. The reaction was evaporated to give a brown oil which was taken into 1:1 ethyl acetate: n-hexane. The precipitate was filtered off and the filtrate was washed two times with dilute HCl (agueous), two times with 1N Na2CO3 (agueous), once with saturated NaCl (agueous), dried over MgSO4, filtered and evaporated to give an oil. The majority of the impurities were removed by flash chromatography (silica gel, 5–10% ethyl acetate:n-hexane). Final purification was achieved using a 3.0×100 cm silica gel column eluted with 7% ethyl acetate:n-hexane. A pure fraction contained 7.8 g, 19% of the desired product. $^1$H-NMR (CDCl3): δ7.05 (s,10H); 5.0 (d,2H); 4.9 (s,2H); 4.1 (m,1H); 2.2 (s,2H); 1.9–1.0 (m,18H); 1.4 (s,9H).

(3) 2-L-Boc-amino-6-[(1-carbobenzoxymethyl)cyclohexyl]hexanoic acid.

1N NaOH (agueous) (18 ml) was slowly added to benzyl-2-L-Boc-amino-4-(1-carbobenzyoxymethyl)-cyclohexylhexanoate (7.6 g, 13.8 mmol) in dioxane (32 ml) with stirring at room temperature. After stirring overnight the reaction was taken up in water acidified with 1N HCl then extracted two times with ethyl acetate. The ethyl acetate phases were combined, washed with saturated NaCl (agueous), dried over MgSO4, filtered, and evaporated to given an oil. The product was purified on a silica gel column (3×100 cm) eluted with chloroform methanol, acetic acid (99:1 0.1) to give pure fraction 3.36 g, 53%.

$_1$H-NMR (CDCl3): δ7.05 (s, 5H); 4.95 (br s,1H); 4.9 (s,2H); 4.1 (br s,1H) 2.2 (S, 2H); 1.9–1.0 (m, 18H); 1.4 (S, 9H); Mass spectrum (M+H)+=462.

(D) General

Running the reaction sequence (A) starting with 1,1-cyclopentane diacetic acid gives benzyl 2-L-Boc-amino-5-[(1 carbobenzoxymethyl)cyclopentyl]pentanoate. Running the reaction sequences A, starting with N-α-Boc-D-Glu-α-benzyl ester, N—α—Boc—D—Asp—α—benzyl ester or N-α-Boc D-Glu-α-benzyl ester gives benzyl 2-D-Boc-amino-5[(1-carbobenzoxymethyl)cyclohexyl]pentanoate, 2-D-Boc-amino-4-[(1-carbobenzoxymethyl)-cyclohexyl]butanoic acid or 2-D-Boc-amino-6-[(1-carbobenzoxymethyl)-cyclohexyl]-hexanoic acid respectively.

What is claimed is:

1. A chemical compound having the formula:

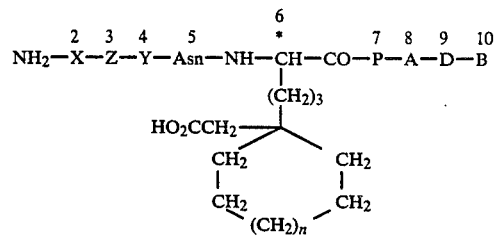

in which:

n is 0 or 1;

P is a single bond or a D or L isomer of Pro, ΔPro, Ala, MeAla, Arg, Lys, HArg, MeArg, MeLys or MeHArg;

A is a single bond, Gly, or a D or L isomer of Arg, Lys, Orn, HArg, MeArg, MeLys, MeOrn, MeHArg or Gln;

D is a single bond, Gly, or a D or L isomer of Arg, Lys, HArg, Me Arg, MeLys, MeHArg, Gln or Orn;

B is OH, NH2, NHAlk or NH (CH2)$_m$NHR;

Z is Phe, Phe(4'—Alk), Tyr(Alk), Ile or Tyr;

X is a D or L isomer of Phe, Phe(4'—Alk), Val, Nva, Leu, Ile, Pba, Nle, Cha, Abu, Met, Chg, Tyr, Trp or Tyr(Alk); and Y is Val, Ile, Abu, Ala, Chg, Gln, Lys, Cha, Nle, Thr, Phe, Leu or Gly;

m is 2 to 6;

R is H or C(=NH)NH2 and

* is to indicate D isomer, L isomer or a D,L mixture

2. The chemical compound of claim 1 in which n is 1, P is a single bond, A is Arg, B is NH2, Z is Phe, X is D—Tyr(Et) and Y is Val.

3. The chemical compound of claim 1 in which n is 1, P is Pro, A is Arg, B is NH2, Z is Phe, X is D Tyr(Et) and Y is Val.

4. The chemical compound of claim 1 in which n is 1 P is Pro, A is Arg, B is Gly(NH2), Z is Phe, X is D—Tyr(Et) and Y is Val.

5. The chemical compound of claim 1 in which n is 1, * is L, P is Arg, A is D—Arg, D is single bond, B is NH2, Z is Phe. X is D—Tyr(Et) and Y is Val.

6. The chemical compound of claim 1 in which n is 1, * is D, P is Arg, A is D—Arg, D is single bond, B is NH2, Z is Phe, X is D—Tyr(Et) and Y is Val.

* * * * *